United States Patent [19]

Shepard

[11] Patent Number: 5,631,465
[45] Date of Patent: May 20, 1997

[54] METHOD OF INTERPRETING THERMOGRAPHIC DATA FOR NON-DESTRUCTIVE EVALUATION

[76] Inventor: Steven M. Shepard, 23656 Hunter's La., Southfield, Mich. 48034

[21] Appl. No.: 608,901

[22] Filed: Feb. 29, 1996

[51] Int. Cl.$^6$ .................................................. G01N 25/72
[52] U.S. Cl. .................... 250/330; 250/358.1; 250/341.6
[58] Field of Search .................................... 250/330, 332, 250/358.1, 341.6

[56] References Cited

U.S. PATENT DOCUMENTS

| | | | |
|---|---|---|---|
| 5,032,727 | 7/1991 | Cox, Jr. et al. | 250/330 |
| 5,250,809 | 10/1993 | Nakata et al. | 250/358.1 |

*Primary Examiner*—Carolyn E. Fields
*Attorney, Agent, or Firm*—Rader, Fishman & Grauer PLLC

[57] ABSTRACT

In connection with a method of interpreting thermographic data for nondestructive evaluation of subsurface structural irregularities in a sample object, the sample object is thermally excited and then allowed to cool. As the thermal energy level on the object's surface changes, a series of positionally-fixed infrared images of the object are acquired. The method calculates a pixel sum set for each image in the series by counting the number of pixels in each image which display each of the different pixel shades of gray (or colors). The mathematical moments of each of the functions derived from the pixel sum sets are then calculated, producing a single total energy value for each image, the total energy values collectively being referred to as a total energy value set. The total energy value set acquired from the sample object is compared to a control total energy value set expected from an infinitely thick, perfectly homogenous object to identify anomalous surface infrared radiation patterns, indicating subsurface structural irregularities in the sample object. Alternatively, instead of taking the mathematical moment of the pixel sum sets, the pixel sum sets themselves may be compared individually to a control pixel sum set expected from an infinitely thick, perfectly homogenous object, likewise identifying anomalous surface infrared radiation patterns.

10 Claims, 3 Drawing Sheets

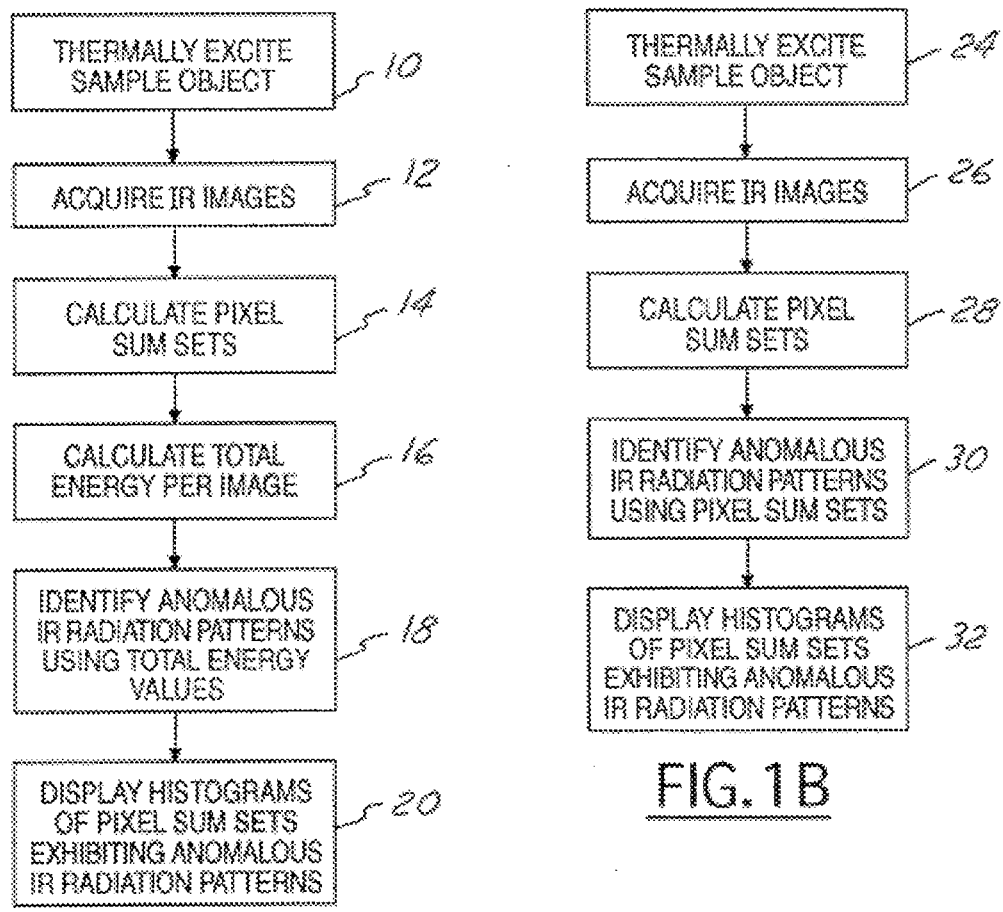
FIG.1A
FIG.1B
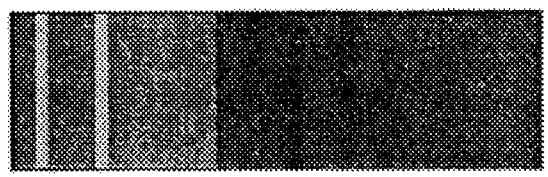
FIG.2A
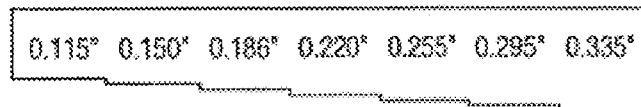
FIG.2B

METHOD OF INTERPRETING THERMOGRAPHIC DATA FOR NON-DESTRUCTIVE EVALUATION

BACKGROUND OF THE INVENTION

1. Field Of The Invention

This invention relates generally to a method of nondestructive evaluation of physical structures, and more particularly to a method of detecting and evaluating subsurface structural irregularities of objects using thermographic images and associated data.

2. Background Of The Art

Infrared (IR) imaging methods have shown considerable promise as techniques for nondestructive evaluation (NDE) of metals, composites, ceramics, and polymers, offering fast, wide area, noncontact detection of delamination, disbonding, corrosion, and voids. However, optimum results obtained with IR techniques existing in the art have generally required considerable sophistication on the part of the operator, particularly in terms of interpretation and understanding of the resulting IR images.

For example, known methods in the art of infrared NDE involve thermally exciting a target object with a heat source, such as a hot air gun, for a finite period of time, thereby imparting thermal energy to the object. After the target object has been thermally excited, the object is allowed to cool, and thermal energy earlier absorbed by the object then begins to dissipate. As the object cools, a series of successive positionally-fixed IR images of the external surface of the object are acquired by an infrared camera. The images are acquired at fixed time intervals, starting relative to the end or the beginning of the thermal excitation period, and continuing during the period while the object cools, until a pre-determined time period has elapsed.

Typically, the infrared camera communicates with a general purpose computer or other video monitor on which the acquired images are displayed. An operator typically performs NDE analysis of the acquired images by either viewing the video output of the infrared camera in real time, or by having the output data stored to videotape or computer memory, where further processing and analysis may take place. Each image is comprised of a collection of gray-scale (or color) pixels, each pixel corresponding to a specific position on the object's external surface. The amplitude of each pixel, i.e. each distinct shade of gray (or different color) exhibited by the different pixels represents a different thermal energy level associated with the pixel's corresponding position on the object's external surface. Known methods of analysis can be broadly categorized as either visual analysis—where the operator views the image sequence taken during or after heating, watching for changes in the scene which correspond to effects due to subsurface structural irregularities—or temporal analysis—where the behavior of each pixel in the scene is analyzed as a function of time, and changes in slope or amplitude of each pixel over time are correlated to the effects of local subsurface structural irregularities.

The visual method depends upon the ability of an operator to identify anomalous changes in the scene from one image to the next merely by visually inspecting the many thousands of pixels which comprise each and every image. Though widely used as one of the existing alternatives in NDE analysis, the visual method is inherently qualitative and imprecise, since the ability of the operator to identify anomalous changes in the scene depends on subjective factors such as the colors assigned to various temperatures, the quality of the display device, and the experience of the operator. Furthermore, the mere fact that the visual method requires an operator to manually inspect each acquired image makes this method labor intensive and time-consuming.

The temporal method, on the other hand, which can sometimes be more precise than the visual method, is extremely computation intensive and frequently requires that high-resolution, high-speed IR cameras be used in order to acquire sufficient data to determine the accurate shape of the temperature time curve for each pixel of each image and the exact time at which the peak or peak slope of each curve occurs. While more objective and precise than the visual method, the temporal method is not commercially viable due to the high cost of high-resolution, high-speed IR imagers and the computer hardware requirements to perform the necessary complex computations.

Accordingly, there is a need to provide an objective and quantifiable method of NDE analysis which does not require an inordinate amount of complex computations and thus overly expensive hardware.

SUMMARY OF THE INVENTION

It is the objective of this invention to provide a method for interpretation of thermographic data for purposes of nondestructive evaluation of subsurface structural irregularities in a sample object. A preferred embodiment of the present invention accomplishes this objective by thermally exciting a sample object and acquiring a series of positionally-fixed infrared images of the object over a fixed period of time while the object is being heated and/or allowed to cool. We see that in response to uniform heating, sample objects having subsurface structural irregularities exhibit non-uniform surface temperature patterns. Information about the depth and composition of these subsurface structural irregularities can be obtained by analyzing the timing of the infrared energy which is radiated from the object's surface as detected by an IR camera. The method of this invention requires calculation of a pixel sum set for each image in the series by counting the number of pixels which display each of the different pixel shades of gray (or colors). With reference to the pixel sum sets, anomalous surface temperature patterns of the sample object are identified, and graphical representations of the pixel sum sets associated with such anomalous surface temperature patterns may be displayed to an operator if desired.

These and other features and objects of this invention will become apparent to one skilled in the art from the following detailed description and the accompanying drawings illustrating features of this invention by way of example.

BRIEF DESCRIPTION OF THE DRAWINGS

FIG. 1A is a simplified flow chart illustrating the steps performed by the preferred embodiment of the present invention.

FIG. 1B is a simplified flow chart illustrating the steps performed by an alternative embodiment of the present invention.

FIG. 2A is a simplified representative gray-scale infrared image of the sample object illustrated in FIG. 2B.

FIG. 2B is a simplified cross-sectional view of a 10–18 carbon steel bar machined to indicated thicknesses used as a sample object.

DESCRIPTION OF THE PREFERRED AND ALTERNATIVE EMBODIMENTS

Figure 3A:
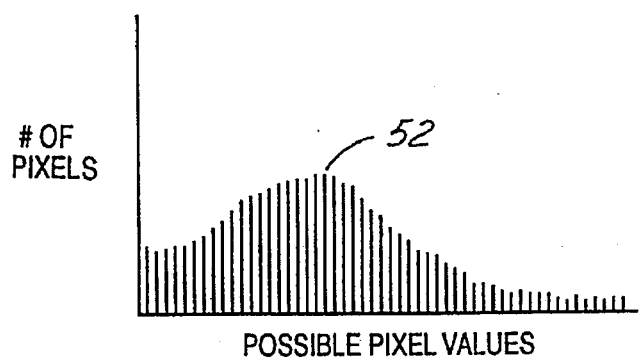
FIG. 3A is a simplified histogram representation of a typical pixel sum set for a sample object in a state of thermal equilibrium.

The present invention relates to an NDE method of detecting subsurface structural properties of an object through analysis of data gathered from a series of thermal images of the object. The present invention exploits the fact that when an infinitely thick, perfectly homogenous object is actively heated, the radiation of infrared energy from the object's surface occurs in a predictable manner. An anomalous infrared radiation pattern detected on the external surface of the object indicates a subsurface structural irregularity in the object. Specifically, the surface of an infinitely thick, perfectly homogenous object cools monotonically. Subsurface structural irregularities in the object cause unexpected sudden changes in the infrared radiation from the object's surface due to reflection of dissipating thermal waves. Anomalous surface infrared radiation patterns can be detected by evaluating data derived from a series of positionally-fixed infrared images of the object taken over a predetermined period of time. The exact location of a subsurface irregularity can be determined by examining the particular two-dimensional infrared image acquired at the time when the anomaly in the infrared radiation from the object's surface occurred and analyzing the elapsed time from the beginning of the predetermined time period.

FIG. 1A and FIG. 1B illustrate steps involved in alternative embodiments of the invention. It should be noted that the steps involved in each embodiment are identical except for those steps 16, 18, and 30 which are specific to the analysis process of the acquired images. According to the preferred embodiment of the invention illustrated in FIG. 1A, as well as an alternative embodiment illustrated in FIG. 1B, thermal energy is imparted to the object, steps 10, 24. Many different well-known sources of heat may be used to perform the thermal excitation, including flashlamps, stepped heat lamps, hot air, and electromagnetic induction. Subsequent to the thermal excitation, the object is allowed to cool, during which time a positionally-fixed infrared camera acquires a series of infrared images of an external surface of the object, steps 12, 26. As an alternative, the series of positionally-fixed infrared images may be acquired during the heating process, provided that the chosen method of heating occurs over a sufficiently long enough time period to acquire several infrared images. As a further alternative, the series of positionally fixed infrared images may be required during a time period spanning both the heating process and the cooling process. Any of these methods of acquiring the series of infrared images will be satisfactory for purposes of this invention.

Depending on the method employed, the images are acquired at fixed time intervals (e.g. at times t1, t2, t3, ... tn) for a pre-determined time period either during the cooling process, during the heating process, or across both time periods. FIG. 2A illustrates a single representative IR image of a sample object illustrated in FIG. 2B. Each image is comprised of a collection of pixels, each pixel corresponding to a specific physical position on the external surface of the object. Each pixel is further associated with a pixel index value, which is indicative of the shade of gray or the color displayed by that pixel in the acquired image. The different shades of gray (or different colors) and thus the associated pixel index values, represent different thermal energy levels existing on the external surface of the object. While the capabilities of the employed IR camera hardware is determinative of the total possible number of pixel index values per pixel, and thus the total possible shades of gray (or colors) per pixel, the IR camera employed in the constructed embodiment is capable of acquiring a 12-bit image, thereby being capable of displaying 4096 different shades of gray or different colors.

After all images have been acquired, certain data from each of the images are extracted and organized. Specifically, for each possible pixel index value for each acquired image, the number of pixels in each acquired image having that particular pixel index value are separately counted and stored, each individual such sum being referred to as a "pixel sum." Thus, each possible pixel index value for each acquired image is associated with a single pixel sum. All pixel sums associated with a single image are referred to collectively as pixel sum sets, steps 14, 28. For example, in the preferred embodiment, for each individual image, the number of pixels having a pixel index of 1 are counted and stored, such sum being referred to as pixel sum 1. The same process is completed for each pixel index value through pixel index value 4096. Pixel sums 1 through pixel sum 4096 for the same image are referred to together as a pixel sum set. A similar pixel sum set is calculated for each acquired image. Then, each pixel sum set is portrayed as a graphical histogram, as illustrated in FIGS. 3A–3D, as a function of possible pixel index values, with the X-axis representing the possible pixel index values (in this example, 4096) and the Y-axis representing the number of pixels having the corresponding pixel index value. Ultimately, each IR image is associated with a corresponding histogram.

Figure 3B:
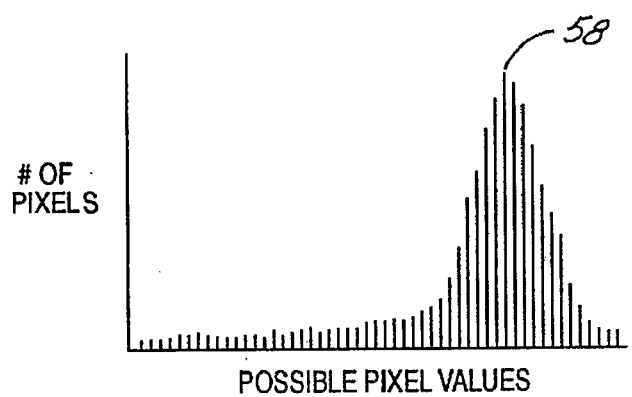
FIG. 3B is a simplified histogram representation of a typical pixel sum set immediately after the target object has been thermally excited.
Figure 3C:
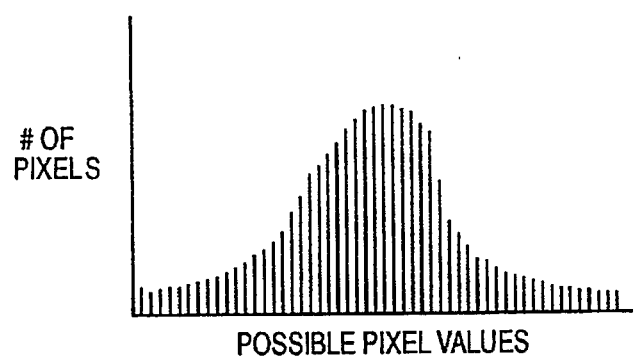
FIG. 3C is a simplified histogram representation of a typical pixel sum set of an infinitely thick, perfectly homogenous sample object acquired at a time while the object was either being heated or cooled.
Figure 3D:
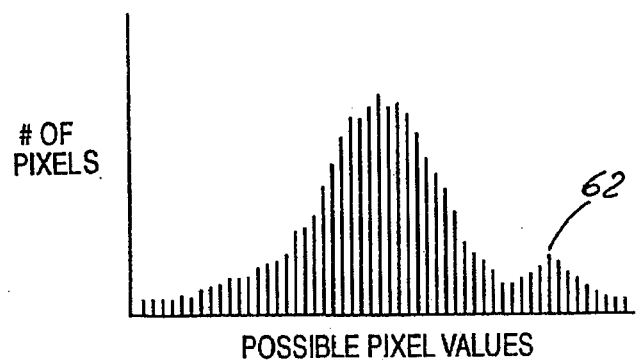
FIG. 3D is a simplified histogram representation of a pixel sum set acquired from an object exhibiting a subsurface structural irregularity while the object was either being heated or cooled.

FIG. 3A illustrates a histogram representation of a typical pixel sum set for a sample object prior to any thermal excitation, the X-axis representing the different possible pixel index values and the Y-axis representing the number of pixels having each pixel index value. As can be seen in FIG. 3A, the histogram displays an approximately Gaussian distribution with a primary relative maximum, 52, at the lower energy values. The higher energy values are only sparsely populated. FIG. 3B illustrates a histogram representation of a typical pixel sum set immediately after thermal excitation and prior to cooling. Thermal excitation of the object causes the distribution of intensity values to shift to the right (higher energy values) and the primary relative maximum, 58, to increase. As can be seen in FIG. 3B, the primary relative maximum, 58, is sharper than in FIG. 3A and shifted toward higher energy values. FIG. 3C illustrates a histogram representation of a typical pixel sum set of an infinitely thick, perfectly homogenous sample object acquired at a time during the object's cooling process. As can be seen in FIG. 3C, the Gaussian distribution begins to broaden and shift back toward lower energy values as the histogram tends toward its pre-excitation equilibrium shape. FIG. 3D illustrates a histogram representation of a pixel sum set acquired from an object exhibiting a subsurface structural irregularity after thermal excitation and as that object cools. FIGS. 3C and 3D also illustrate histogram representations of pixel sum sets acquired from an object exhibiting a subsurface shape of the structural irregularity during the thermal excitation period, as the histogram of the cooling process is similar to that of the heating process. As can be seen in FIG. 3D, energy returned to the surface of the object by reflection of thermal waves by a subsurface structural irregularity gives rise to a secondary relative maximum, 62, in the histogram regardless of whether the object is undergoing heating or cooling. Multiple secondary relative maximums, 62, may occur in a histogram, and each secondary relative maximum, 62, corresponds to a particular subsurface structural irregularity.

In the preferred embodiment of the invention illustrated in FIG. 1A, a total energy value, representing the total thermal energy associated with the external surface of the object, is calculated for each image, step 16. Thus, each calculated total energy value corresponds to the total energy level associated with the object's external surface at a particular time, such as time t1, during the cooling process or during the heating process. In the preferred embodiment, the total energy value is determined by calculating the mathematical moment of the image's pixel sum set as a function of possible pixel index values, i.e. for each pixel sum set, summing together all of the pixel sums corresponding to the respective pixel index values. Finally, all of the total energy values (one for each image) are grouped together as a total energy set. Subsurface structural irregularities are identified by comparing the characteristics of this total energy set to the expected characteristics of a total energy set for an infinitely thick, perfectly homogenous object, step 18.

Figure 4A:
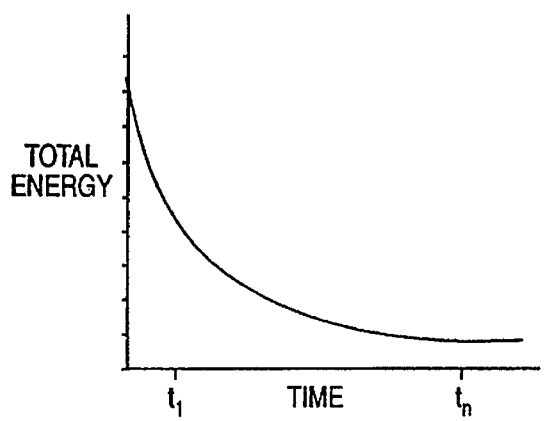
FIG. 4A is a simplified graphical representation of a sample total energy set displayed as a function of time for an infinitely thick, perfectly homogenous object, acquired while the object was cooling.
Figure 4B:
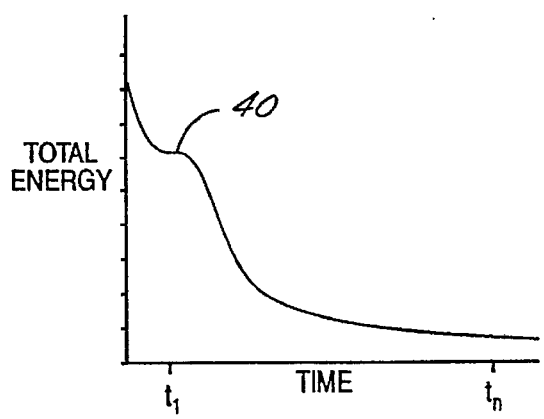
FIG. 4B is a simplified graphical representation of a sample total energy set for an object having a subsurface structural irregularity, acquired while the object was cooling.
Figure 5A:
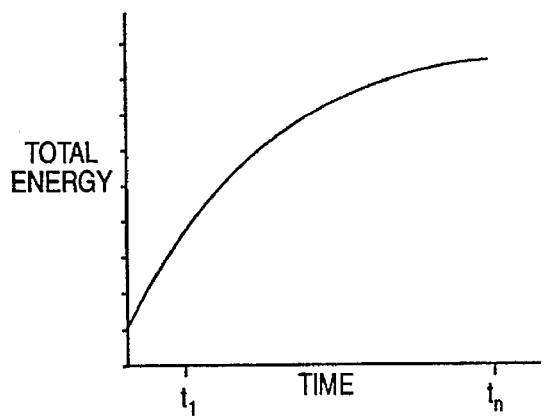
FIG. 5A is a simplified graphical representation of a sample total energy set displayed as a function of time for an infinitely thick, perfectly homogenous object, acquired while the object was being heated.
Figure 5B:
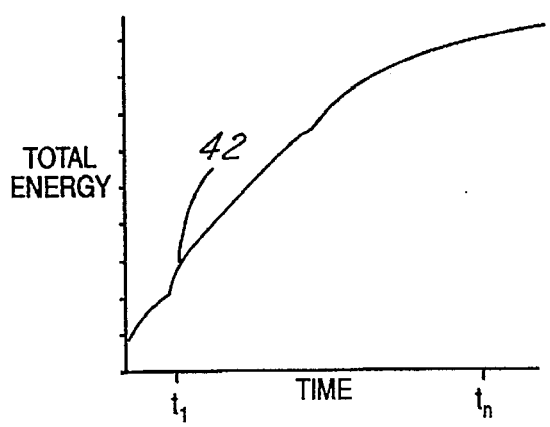
FIG. 5B is a simplified graphical representation of a sample total energy set for an object having a subsurface structural irregularity, acquired while the object was being heated.

FIG. 4A illustrates a graphical representation of a sample total energy set displayed as a function of time for an infinitely thick, perfectly homogenous object acquired while the heated sample object was cooling. As can be seen from FIG. 4A, the resulting curve decays monotonically, since the deposited thermal energy is lost through either conduction to the bulk, convection, or radiation. FIG. 4B, in contrast, illustrates a graphical representation of a sample total energy set for an object having a subsurface structural irregularity, such total energy set being acquired while the object was cooling. As can be seen from FIG. 4B, subsurface obstructions to the flow of heat cause thermal energy to be returned to the surface at a finite time after initial heating, which causes a corresponding anomaly 40 in the infrared radiation on the object's surface. The times corresponding to an anomaly, 40, are the times at which the corresponding subsurface structural irregularities can be seen in the IR image sequence. FIG. 5A and FIG. 5B illustrate the counterpart graphical representations to FIGS. 4A and 4B of the total energy sets acquired while the same sample object was heated instead of while it cooled. As can be seen in FIG. 5B, an anomaly 42 similar to anomaly 40 occurs at about the same time in the total energy graph due to reflection of thermal waves back to the object's surface caused by subsurface irregularities.

In the preferred embodiment of this invention, the anomalies, 40, 42, are identified numerically using a personal computer to calculate the second derivative of the total energy values as a function of time for each image to determine if there is a noticeable anomaly in the object's surface infrared radiation. If the second derivative demonstrates unexpected behavior for a particular time in the sequence, then a subsurface irregularity is detectable on the IR image acquired at that particular time. Alternatively, anomalies, 40, 42, can be identified by visual inspection by an operator of the histograms as illustrated in FIGS. 3A–3D. Each anomaly, 40, 42, directly corresponds to a unique IR image and corresponding histogram, each exhibiting evidence of subsurface structural irregularities in the object.

After all of the anomalies, 40, 42, are identified, the histograms corresponding to the secondary relative maximums, 62, may be displayed to an operator for examination and analysis purposes, step 20. For each displayed histogram, the portion of the displayed histogram corresponding to the subsurface structural irregularity, i.e., the secondary maximum, 62, is highlighted to the operator. Alternatively, a computer can be programmed to take certain actions independent of a human operator based on the identification of subsurface irregularities existing in the object. For example, a computer may be programmed to reject certain parts on an assembly line that show evidence of a subsurface structural irregularity.

In the alternative embodiment of this invention illustrated in FIG. 1B, images which exhibit anomalous infrared radiation patterns are identified by analyzing the pixel sum sets themselves, which are graphically illustrated by the histograms in FIGS. 3A–3D, instead of taking the further step, as in the preferred embodiment, of calculating a total energy value set. In the alternative embodiment of the invention, the pixel sum sets are calculated as detailed above and as illustrated in step 28, but the total energy values are not calculated. Instead, after the pixel sum sets are calculated, the characteristics of each pixel sum set are compared individually to the expected characteristics of a corresponding pixel sum set for an infinitely thick, perfectly homogenous object to identify which images demonstrate evidence of surface or subsurface material irregularities, step 30. As discussed above, pixel sum sets, and their corresponding histograms, which exhibit secondary maximums, 62, correspond to IR images which show evidence of some subsurface irregularity.

In the alternative embodiment of the invention illustrated in FIG. 1B, each pixel sum set is analyzed individually to determine if it exhibits one or more secondary relative maximums, 62. This determination can be made numerically, either manually by an operator or through the use of a general purpose computer, by comparing each pixel index value to its immediate previous and immediate subsequent pixel index value. Alternatively, this determination can be made by an operator visually inspecting the histogram representations of the pixel sum sets similar to those illustrated in FIGS. 3A–3D. Finally, the IR images corresponding to the histograms exhibiting one or more secondary maximums 62, may be displayed to an operator, step 32, in which case the secondary maximums 62, are highlighted to the operator. Alternatively, as stated earlier, a computer may programmed to take action independent of any human operator based on the described identification.

The described invention exhibits many advantages over the prior art. First, the described method is computationally simple, mostly involving just counting and sorting operations. The computational simplicity of the described method alleviates the necessity for high-powered computers to perform the operations. Second, by amassing a database of histograms and total energy curves acquired from "good" samples, the described method can be implemented to consecutively evaluate a succession of objects and make certain decisions based on the results of the evaluations without the need for human intervention. Third, the described method, by examining the aggregate behavior of a large number of pixels without resorting to curve smoothing or averaging techniques, demonstrates a significantly better ability to detect and separate a signal due to background noise while not diluting the behavior of each individual pixel. Finally, because of its computational simplicity, the described method could be used as a preprocessor for the more complicated infrared NDE methods known in the art by limiting the set of pixels to be inspected by the more complicated method, thus reducing the amount of required complicated computations.

The preceding description is exemplary rather than limiting in nature. A preferred embodiment of this invention has been disclosed to enable one skilled in the art to practice this invention. Variations and modifications are possible without departing from the spirit and purview of this invention, the scope of which is limited only by the appended claims.

I claim:

1. A method of nondestructive evaluation of subsurface structural properties of an object, comprising the steps of:

irradiating a surface of said object thereby creating an irradiated surface to which thermal energy is imparted to said object;

acquiring a series of positionally fixed 2-dimensional thermal images from an emissive surface of said object, wherein successive said images are acquired at successive times during a fixed time period as the level of thermal energy present on said emissive surface changes, each said image having a plurality of pixels, each said pixel corresponding to a unique position on said emissive surface, wherein each said pixel is associated with a corresponding finite index value which is related to a measurement of a thermal energy level associated with said pixel's corresponding position on said emissive surface;

summing, for each possible said index value of each individual said image, the number of said pixels associated with each said possible index value of said image, establishing for each image a pixel sum set; and determining, with reference to said pixel sum sets, which of said images was acquired at a time when said emissive surface exhibited an anomalous infrared radiation pattern.

2. The method defined in claim 1, wherein said emissive surface and said irradiated surface are the same surface.

3. The method defined in claim 1, wherein said irradiating step is accomplished by flash heating.

4. The method defined in claim 1, further comprising the step of displaying one or more graphical representations of said pixel sum sets as functions of said possible index values, each said displayed graphical representation corresponding to one said image which was acquired at a time when said emissive surface exhibited an anomalous thermal energy radiation pattern.

5. The method defined in claim 1, wherein said determining step comprises the substeps of:

displaying, for each said pixel sum set, a graphical representation of corresponding said pixel sums as a function of said possible index values; and identifying, through visual inspection of said graphical representations, all of said graphical representations which individually exhibit one or more secondary relative maximums.

6. The method defined in claim 1, wherein said determining step comprises the substeps of:

comparing, for each said pixel sum set, each said pixel sum, except first said pixel sum and last said pixel sum, to immediate previous said pixel sum and immediate subsequent said pixel sum to determine each relative maximum pixel sum, said relative maximum pixel sum being greater than or equal to said immediate previous said pixel sum and also greater than or equal to immediate subsequent said pixel sum; and identifying all said images corresponding to a pixel sum set exhibiting more than one relative maximum.

7. The method defined in claim 1, wherein said determining step comprises the substeps of:

calculating, for each individual said image, a total energy value representing a total thermal energy level existing on said emissive surface;

displaying a graphical representation of said total energy values as a function of time; and identifying, through visual inspection, all images which correspond to a time point on said graphical representation wherein corresponding said total energy value exhibits an anomalous change in comparison to relative total energy values.

8. The method defined in claim 7, wherein said calculating step is performed by calculating for each said pixel sum set, the mathematical moment of said pixel sums as a function of said possible index values.

9. The method defined in claim 1, wherein said determining step comprises the substeps of:

calculating, for each individual said image, a total energy value representing a total thermal energy level existing on said emissive surface; and identifying, through numerical analysis, all said images which individually correspond to respective total energy values which exhibit an anomalous change in infrared radiation in comparison to relative total energy values.

10. The method defined in claim 9, wherein said identifying substep comprises the further substeps of:

calculating the mathematical second derivative of said total energy values as a function of time for each said image; and identifying time points at which said second derivative displays anomalous behavior.

\* \* \* \* \*